(12) United States Patent
Liu et al.

(10) Patent No.: US 11,198,840 B2
(45) Date of Patent: Dec. 14, 2021

(54) ASSEMBLED BIOREACTOR CHAMBER SUITABLE FOR PERFUSION CULTURE

(71) Applicant: Jiangyin Recongene Biomedical Technologies Co., Ltd., Jiangsu (CN)

(72) Inventors: Qing Liu, Jiangyin (CN); Xiao Meng, Jiangyin (CN)

(73) Assignee: Nanjing Recongene Biomedical Technologies, Inc., Nanjing (CN)

( * ) Notice: Subject to any disclaimer, the term of this patent is extended or adjusted under 35 U.S.C. 154(b) by 296 days.

(21) Appl. No.: 16/060,336

(22) PCT Filed: Dec. 18, 2015

(86) PCT No.: PCT/CN2015/097855
§ 371 (c)(1),
(2) Date: Jun. 7, 2018

(87) PCT Pub. No.: WO2017/101096
PCT Pub. Date: Jun. 22, 2017

(65) Prior Publication Data
US 2019/0031989 A1  Jan. 31, 2019

(51) Int. Cl.
*C12M 1/20* (2006.01)
*C12M 1/00* (2006.01)
(Continued)

(52) U.S. Cl.
CPC ............... *C12M 1/20* (2013.01); *C12M 3/00* (2013.01); *C12M 23/44* (2013.01); *C12M 23/46* (2013.01);
(Continued)

(58) Field of Classification Search
None
See application file for complete search history.

(56) References Cited

U.S. PATENT DOCUMENTS 5,057,221 A * 10/1991 Bryant .................. C02F 3/06
210/610
5,240,854 A   8/1993 Berry et al.
(Continued)

FOREIGN PATENT DOCUMENTS

CN   1290744 A   4/2001
CN   2813625 Y   9/2006
(Continued)

OTHER PUBLICATIONS

Machine translation of CN 102127638 provided by USPTO, Li et al, 2011. (Year: 2011).*
(Continued)

*Primary Examiner* — Holly Kipouros
(74) *Attorney, Agent, or Firm* — Christensen O'Connor Johnson Kindness PLLC (57) ABSTRACT

Provided is an assembled bioreactor chamber comprising an upper end portion, at least one intermediate portion and a lower end portion for forming a chamber of the reactor chamber. The upper end portion and the lower end portion are respectively provided with an interface connected with a culture medium line, and the upper end portion and the intermediate portion, and the intermediate portion and the lower end portion are detachably connected in a sealed manner through a connecting mechanism; when the number of the intermediate portions is ≥2, the adjacent intermediate portions are detachably connected in a sealed manner through a connecting mechanism; and the chamber also comprises a cell carrier for cell attachment growth.

20 Claims, 7 Drawing Sheets

(51) Int. Cl.
*C12M 3/00* (2006.01)
*C12M 1/34* (2006.01)

(52) U.S. Cl.
CPC ............ *C12M 23/58* (2013.01); *C12M 29/10* (2013.01); *C12M 41/32* (2013.01); *C12M 41/44* (2013.01)

(56) References Cited

U.S. PATENT DOCUMENTS

| | | | |
|---|---|---|---|
| 6,197,573 B1 * | 3/2001 | Suryanarayan | C12M 21/16 435/286.7 |
| 2010/0075293 A1 | 3/2010 | Chang et al. | |
| 2013/0196375 A1 * | 8/2013 | Strobbe | C12M 23/44 435/69.4 |
| 2014/0193901 A1 * | 7/2014 | Lee | C12M 25/18 435/325 |
| 2014/0323694 A1 * | 10/2014 | Von Keitz | B01J 16/005 530/350 |
| 2015/0079584 A1 * | 3/2015 | Gevaert | C12N 5/0062 435/6.1 |

FOREIGN PATENT DOCUMENTS

| | | |
|---|---|---|
| CN | 102057033 A | 5/2011 |
| CN | 102127638 A | 7/2011 |
| CN | 104039947 A | 9/2014 |
| JP | 2004-147555 A | 5/2004 |
| WO | 03/085080 A1 | 10/2003 |
| WO | WO-2010032260 A1 * | 3/2010 ............ C12M 27/22 |

OTHER PUBLICATIONS

International Preliminary Report on Patentability dated Jun. 19, 2018, issued in corresponding International Application No. PCT/CN2015/097855, filed Dec. 18, 2015, 12 pages.

International Search Report and Written Opinion dated Sep. 27, 2016, issued in corresponding International Application No. PCT/CN2015/097855, filed Dec. 18, 2015, 17 pages.

Chinese Search Report dated Nov. 10, 2020, issued in Chinese Application No. 2015800829949, filed Dec. 18, 2015, 7 pages.

* cited by examiner

ASSEMBLED BIOREACTOR CHAMBER SUITABLE FOR PERFUSION CULTURE

TECHNICAL FIELD

The present invention relates to a bioreactor chamber, and more particularly, to an assembled bioreactor chamber suitable for perfusion culture.

BACKGROUND ART

In perfusion culture, cells are added into a reactor together with a culture medium. During the process of cell growth and product formation, the culture medium under some conditions is continuously removed, and new culture medium is continuously perfused. The commonly used bioreactors in perfusion culture mainly include the following two types.

One type is a stirred bioreactor for suspended cell culture. This type of reactor needs to have a cell retention system (or device). Initially, a microporous membrane filtration system or a rotary membrane system was generally used as the cell retention system. Recently, various types of sedimentation systems or dialysis systems have recently been developed and used. Among them, the hollow fiber bioreactor is a commonly used reactor for continuous perfusion culture. Hollow fiber bioreactors use hollow fiber semi-permeable membranes, through which products and substrates with a small molecular weight can penetrate, and cells and products having a relatively large molecular weight are retained, thereby retaining most cells in the reactor during the continuous perfusion culture process. In recent years, hollow fiber bioreactors have been widely used for the production of product-secreting animal cells, and in particular, they are mainly used for culturing hybridoma cells to produce monoclonal antibodies.

Another type of bioreactor is a fixed bed or fluidized bed bioreactor. Fixed bed bioreactors are equipped with a fixed basket in the reactor, and the middle of the basket is filled with a polyester fiber carrier. Cells can attach to the carrier for growth, or they can also be fixed between the carrier fibers. On the other hand, the negative pressure generated by a gas distributor allows the culture medium to continuously flow through the filler, thereby facilitating the transfer of nutrients and oxygen. This type of fixed bed bioreactor has a higher perfusion rate, and cells grow at a high density in the carrier. The fluidized bed bioreactor keeps the solid particles in a suspending state to react by means of ascending motion of a fluid, and is suitable for the cultivation of immobilized cells.

However, both of these bioreactors have their limitations. For example, currently used bioreactor chambers and their preparation methods mainly have the following disadvantages:

(1) The size of the reactor is specified or fixed. If the amount of the cell culture medium or the quantity of cell cultures is to be changed, it is necessary to repurchase reactors with other sizes or specifications, thereby increasing costs; and the volume cannot be increased or decreased as desired between specifications.

(2) It is not easy to observe the cell growth in the reactor chamber and on the fiber carrier.

(3) The designed fluid direction in the reactor chamber is fixed.

SUMMARY

Therefore, in order to at least partially avoid the above disadvantages, the present invention provides a novel assembled bioreactor chamber that can selectively increase or decrease the volume of the bioreactor chamber.

The present invention provides an assembled bioreactor chamber suitable for perfusion culture, said bioreactor chamber comprising an upper end portion, at least one intermediate portion and a lower end portion which are successively connected, and said upper end portion, said at least one intermediate portion and said lower end portion forming a chamber of the assembled bioreactor chamber, wherein said upper end portion is provided with an upper end portion interface for connecting with a culture medium line, said lower end portion is provided with a lower end portion interface for connecting with a culture medium line, and the upper end portion and the intermediate portion are detachably connected in a sealed manner through a connecting mechanism, the intermediate portion and the lower end portion are detachably connected in a sealed manner through a connecting mechanism, and when the number of the intermediate portions is 2, the adjacent intermediate portions are detachably connected in a sealed manner through a connecting mechanism.

The assembled bioreactor chamber according to the present invention, wherein said upper end portion and said lower end portion can be same or different in structure. In some embodiments, said assembled bioreactor chamber comprises two same end portions and at least one intermediate portion. In other embodiments, said assembled bioreactor chamber comprises an upper end portion, a lower end portion and at least one intermediate portion, wherein said upper end portion and said lower end portion are different in structure.

There is no particular requirement on the upper limit of the number of intermediate portions in the present invention as long as the number of intermediate portions can achieve the object of the present invention.

In some embodiments, the number of intermediate portions of the assembled bioreactor chamber according to the present invention may increase or decrease as desired, for example, depending on the amount of the cell culture medium or the number of cell cultures. In this way, problems such as large investment and inconvenience in use caused by purchasing a single reactor chamber can be avoided.

In some specific embodiments, the number of said intermediate portions is 1-20, preferably 2-20.

In some embodiments, said intermediate portions define the same internal space so that the volume of the assembled bioreactor chamber can increase or decrease in the same volume increment. In other embodiments, the internal space volume of at least part of said intermediate portions is different from one another so that the volume of the assembled bioreactor chamber can flexibly increase or decrease as desired. In some specific embodiments, the number of intermediate portions of the assembled bioreactor chamber according to the present invention is 2, and the assembled bioreactor chamber according to the present invention comprises two kinds of intermediate portions having different internal space volumes. Preferably, the ratio of the internal space volume of one kind of intermediate portion to the internal space volume of the other kind of intermediate portion is from 1:2 to 1:5. More preferably, the ratio of the number of intermediate portions having a larger internal space volume to the number of intermediate portions having a smaller internal space volume is from 1:1 to 1:5.

The assembled bioreactor chamber according to the present invention, wherein the cross section of said chamber may be of any shape, for example, circular, square, rectangular, elliptical, or the like.

The assembled bioreactor chamber according to the present invention, wherein said assembled bioreactor chamber is a fixed bed bioreactor chamber or a fluidized bed bioreactor chamber.

The assembled bioreactor chamber according to the present invention, wherein said assembled bioreactor chamber is a fixed bed bioreactor chamber, said intermediate portion is provided with a basket for supporting cell growth, and said basket is filled with a cell carrier for cell attachment growth, such as a polyester fiber carrier, a polystyrene fiber carrier, a porous polymer material carrier, a porous ceramic material carrier, or the like. In this case, cells can attach to the carrier for growth, or they can also be fixed between the carrier fibers or in the pores. In other cases, a mixture of gel and cells, active biological tissue, etc. may be placed in the basket for cultivation. At the same time, a separate intermediate portion of the reactor can be disassembled to observe the growth of the cells on the carrier in the intermediate portion separately under the microscope.

The assembled bioreactor chamber according to the present invention, wherein said connecting mechanism comprises bolts and nuts for integrally securing said upper end portion, said at least one intermediate portion and said lower end portion.

In some embodiments, said connecting mechanism comprises plug-in slots and plugs which are matched to each other, said plug-in slots and said plugs are provided on the connecting end faces of said upper end portion, said at least one intermediate portion and said lower end portion.

In a preferred embodiment, said plug-in slot extends inwardly and perpendicularly to the end face and shows an L-shape, and said plug extends outwardly and perpendicularly to the end face and shows an L-shape. During assembly, for example, an intermediate portion is pushed towards the lower end portion in the axial direction of the assembled bioreactor chamber, so that the plug is inserted into the plug-in slot, and then the intermediate portion is rotated. Intermediate portions and the upper end portion are successively assembled in accordance with this method.

The assembled bioreactor chamber according to the present invention, wherein the connecting mechanism suitable for the present invention further comprises a fastener provided on the upper end portion, the intermediate portion and the lower end portion.

The assembled bioreactor chamber according to the present invention, wherein the internal structure of the assembled bioreactor chamber can be designed so that the culture medium forms a through flow or forms a zigzag flow within the chamber.

In some embodiments, said assembled bioreactor chamber further comprises at least one barrier sheet for changing the flow direction of the culture medium, said barrier sheet is provided within the chamber and arranged in staggered manner. With the use of the staggered barrier sheet, the culture medium can form a zigzag flow within the chamber. In this case, the cells cultured in each intermediate portion can be brought into contact with the flowing culture medium to the maximum extent.

In some specific embodiments, said barrier sheet can be disposed between the upper end portion and the intermediate portion, between the adjacent intermediate portions, and between the intermediate portion and the lower end portion. In other specific embodiments, said barrier sheet can be integrated onto said intermediate portion.

In a preferred embodiment, the length of said barrier sheet is from 6/10 to 9/10 times, preferably 4/5 times the cross-sectional dimension of the chamber.

In the present invention, the number of barrier sheets may be equal to or less than the number of the intermediate portions.

However, in other embodiments, said assembled bioreactor chamber comprises no barrier sheet, such that the culture medium forms a through flow within the chamber.

The assembled bioreactor chamber according to the present invention, wherein the connecting of the portions in a sealed manner is one in a gas-tight manner or in a liquid-tight manner.

In some embodiments, said assembled bioreactor chamber further comprises sealing rings for connecting the portions in a sealed manner. In the present invention, the number of the sealing rings may be determined according to the number of various portions (including the upper end portion, the intermediate portion, and the lower end portion).

In the present invention, said upper end portion and said lower end portion are designed to have an interface so that they can be connected to a culture medium line. In some embodiments, the upper end portion interface and the lower end portion interface can be directly connected to a culture medium sleeve respectively. In some embodiments, the upper end portion interface and the lower end portion interface can be in the form of a Luer connector.

The assembled bioreactor chamber according to the present invention, wherein, when in use, the assembled bioreactor chamber can be placed in a biological incubator to control its temperature.

The various portions of the assembled bioreactor chamber (for example, the upper end portion, the intermediate portion and the lower end portion) can be prepared by the following methods: first, drawings of the required portions are designed by using computer design software, such as solidworks software, and the required portions are then processed by using machining methods, such as Digital Control Processing Center. In addition to the above methods, the various portions of the assembled bioreactor chamber can also be prepared using other methods known in the art, such as mold opening, injection molding, and 3D printing.

The advantages of the assembled bioreactor chamber according to the present invention are as follows:

1. A bioreactor chamber with a required volume can be freely assembled as desired, for example, according to the amount of cell culture medium or the quantity of cell cultures.

2. The assembled bioreactor chamber of the present invention takes the form of a combination, with each intermediate portion being easily assembled and disassembled.

3. During the cultivation process, the reactor chamber can be opened, and an intermediate portion of interest can be taken out to observe cell growth within the intermediate portion, which can be then assembled again to continue cell culture.

4. The flow path or fluid path can be changed as desired.

BRIEF DESCRIPTION OF FIGURES

Hereinafter, embodiments of the present invention will be described in detail with reference to the accompanying drawings, in which.

BEST MODE FOR CARRYING OUT THE INVENTION

The present invention is described in detail with reference to specific embodiments. The examples are given merely to illustrate the present invention and are not intended to limit the protection scope of the present invention.

Example 1

Referring to FIG. 1 to FIG. 5, these figures show an assembled bioreactor chamber, which comprises an upper end portion 1, a plurality of intermediate portions 2, a lower end portion 3 and sealing rings 6.

The upper end portion 1 is provided with an upper end portion interface 11 for connecting with a culture medium line, and the lower end portion 3 is provided with a lower end portion interface 31 for connecting with a culture medium line. The intermediate portion 2 is provided with a basket for supporting cell growth (not shown), and said basket is filled with a polyester fiber carrier.

The upper end portion 1 and the intermediate portion 2, the intermediate portion 2 and the lower end portion 3, and the adjacent intermediate portions 2 can be detachably connected in a sealed manner through a connecting mechanism. Said connecting mechanism comprises L-shaped plug-in slots 7 and L-shaped plugs 8 which are matched to each other, and bolts 4 and nuts 5 which are matched to each other, and the L-shaped plug-in slots 7 and the L-shaped plugs 8 are provided on the connecting end faces of the upper end portion 1, the intermediate portion 2 and the lower end portion 3. Two plug-in slots 7 and two plugs 8 are respectively provided on each connecting end face, and the plug-in slots and the plugs are arranged at intervals. In addition, the upper end portion 1, the intermediate portion 2 and the lower end portion 3 are provided with holes for mounting the bolts 4.

During assembly, an upper end portion 1, a plurality of intermediate portions 2 and a lower end portion 3 are arranged successively from top to bottom, and a sealing ring 6 is placed between the portions respectively. An intermediate portion 2 is pushed towards the lower end portion 3 in the axial direction of the assembled bioreactor chamber, so that the plugs 8 is inserted into the plug-in slots 7, and then the intermediate portion 2 is rotated. Intermediate portion 2 and the upper end portion 1 are successively assembled in accordance with this method, and then the portions are secured with the bolts 4 and the nuts 5. The upper end portion 1, the plurality of intermediate portions 2 and the lower end portion 3 thereby form a chamber of the assembled bioreactor chamber.

Figure 1:
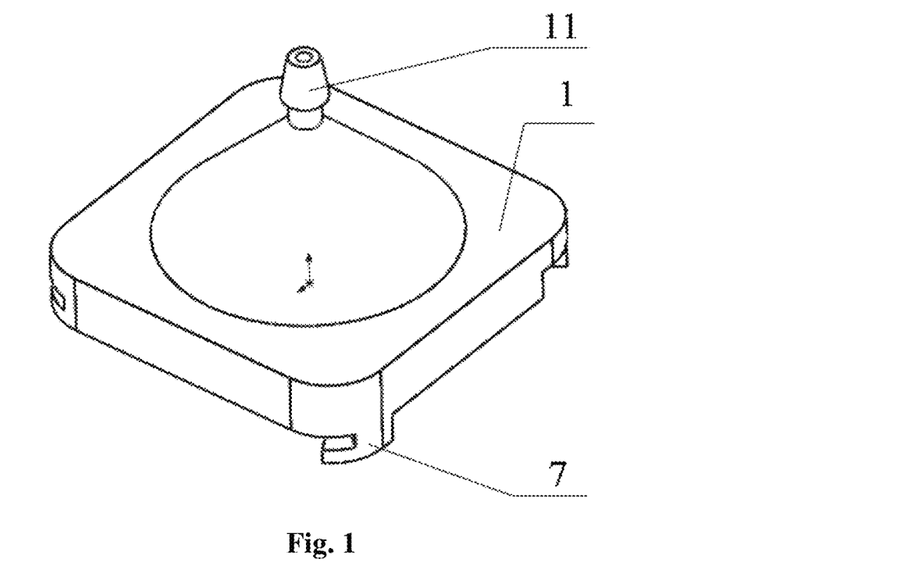
FIG. 1 is a schematic view of an upper end portion of an assembled bioreactor chamber in accordance with one embodiment of the present invention.
Figure 2:
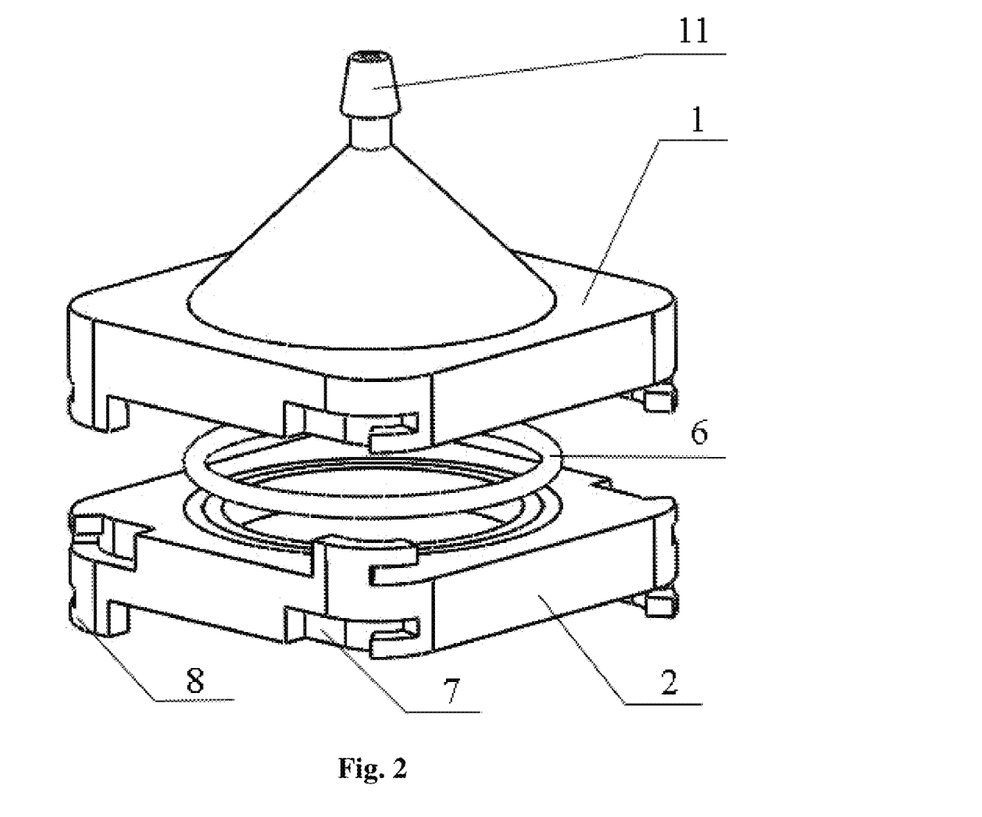
FIG. 2 is a schematic exploded view of an assembled bioreactor chamber in accordance with the present invention, including an upper end portion and an intermediate portion.
Figure 3:
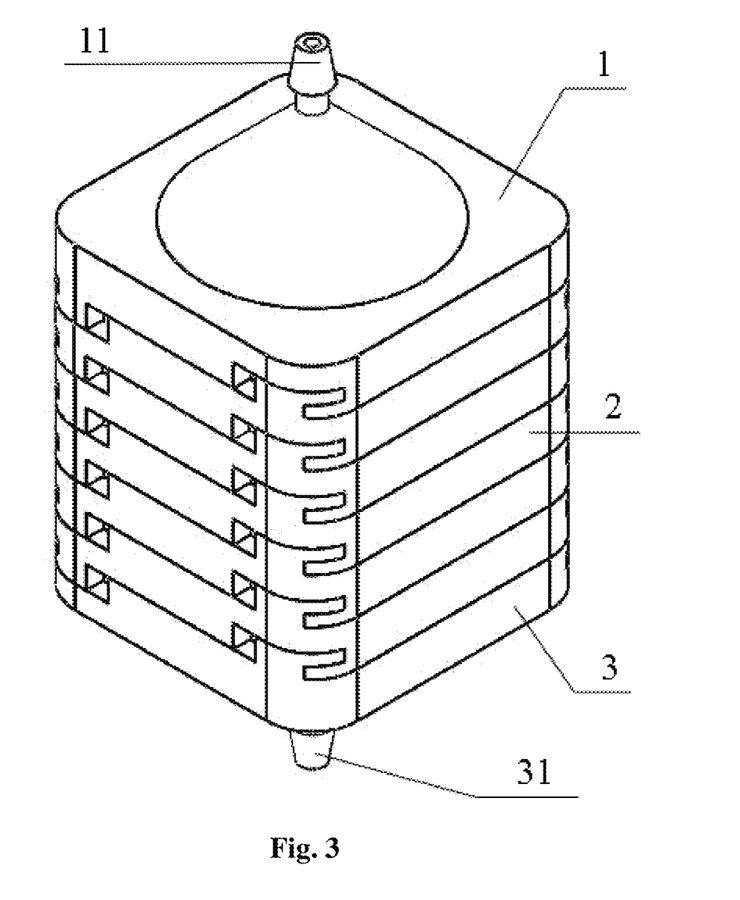
FIG. 3 is a schematic view of an assembled bioreactor chamber in accordance with one embodiment of the present invention.
Figure 4:
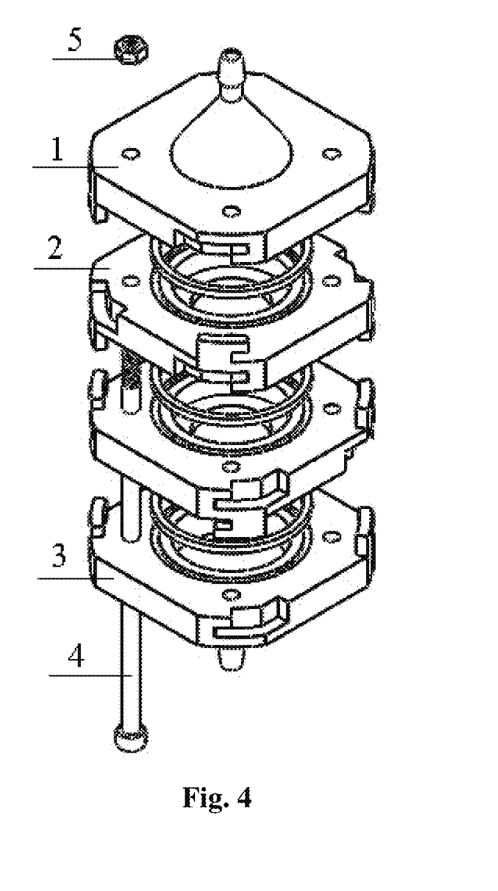
FIG. 4 is a schematic exploded view of an assembled bioreactor chamber in accordance with one embodiment of the present invention.
Figure 5:
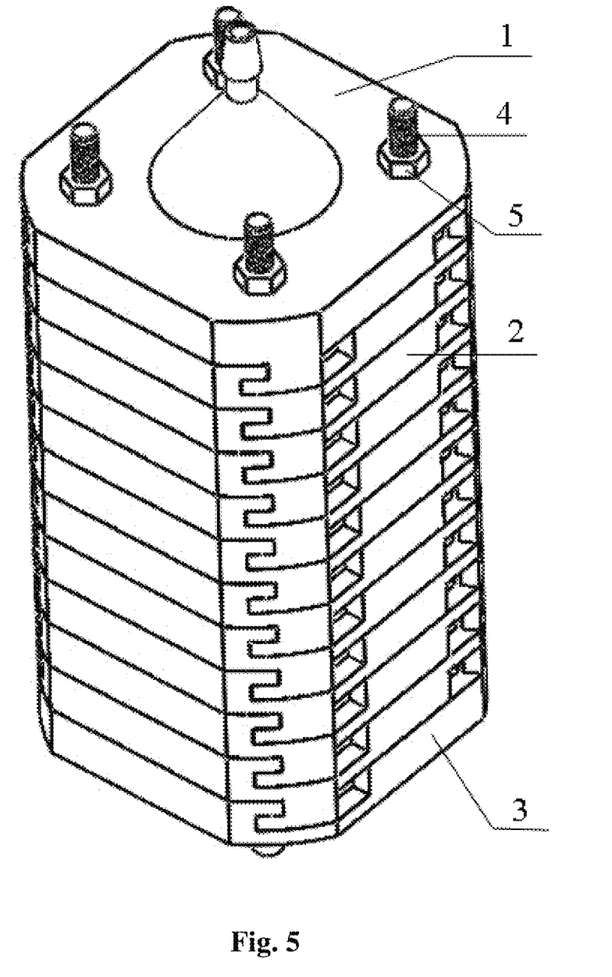
FIG. 5 is a schematic view of an assembled bioreactor chamber in accordance with one embodiment of the present invention after being assembled.
Figure 6:
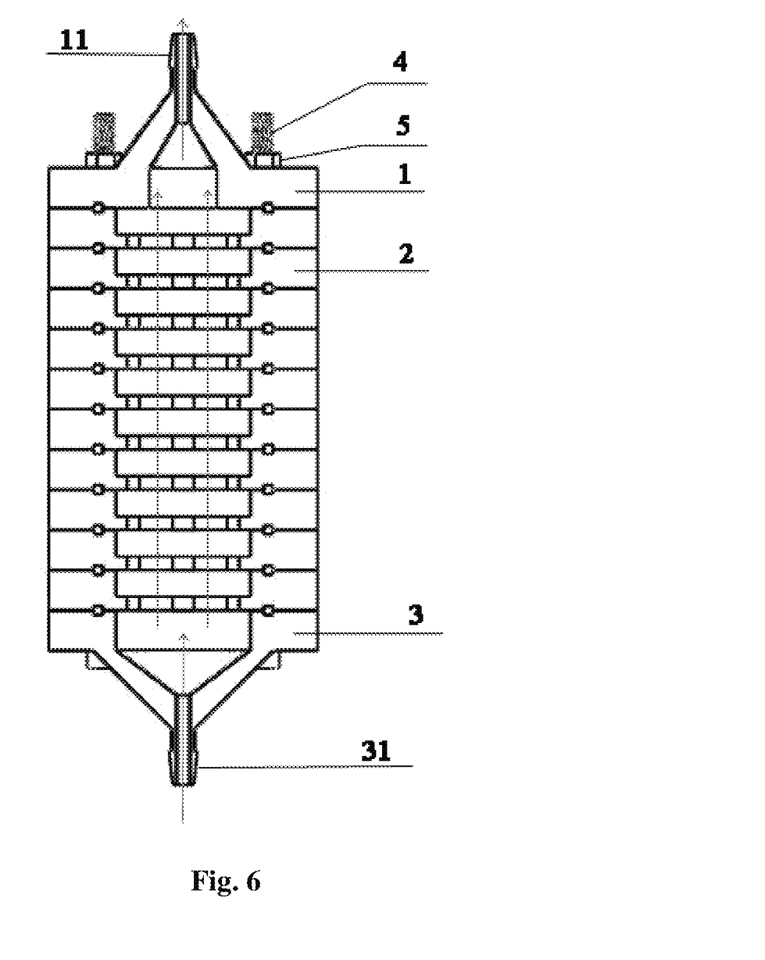
FIG. 6 is a schematic view of the flow state of a culture medium within an assembled bioreactor chamber in accordance with the present invention.

As shown in FIG. 6, in Example 1, the culture medium can form a through flow along the direction indicated by the arrow.

Example 2

Figure 7:
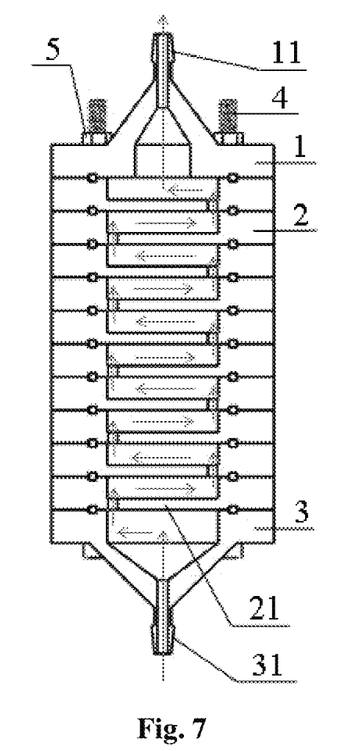
FIG. 7 is a schematic view of another flow state of a culture medium within an assembled bioreactor chamber in accordance with the present invention.

The assembled bioreactor chamber of this Example is substantially the same as that of Example 1, except that the intermediate portion 2 is provided with a barrier sheet 21, and adjacent barrier sheets are arranged in a staggered manner, wherein the length of the barrier sheet 21 is 4/5 times the cross-sectional dimension of the chamber. As indicated by the arrows in FIG. 7, the culture medium can form a zigzag flow in the chamber.

Example 3

Figure 8:
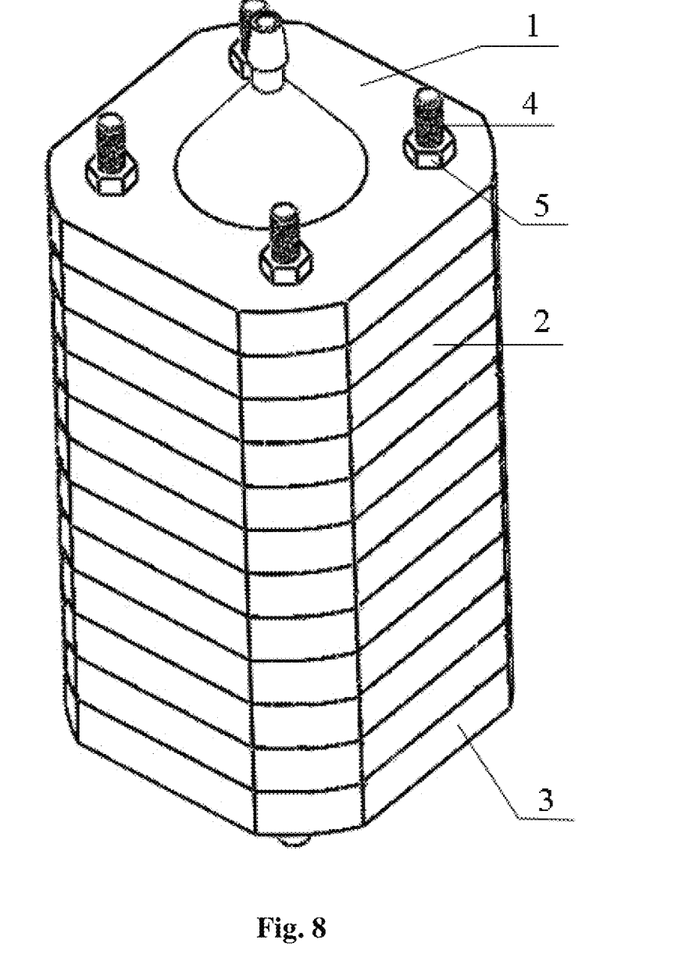
FIG. 8 is a schematic view of an assembled bioreactor chamber in accordance with one embodiment of the present invention after being assembled.

The assembled bioreactor chamber of this Example is substantially the same as that of Example 1, except that said connecting mechanism comprises bolts 4 and nuts 5, and the upper end portion 1, the intermediate portion 2 and the lower end portion 3 are provided with holes for mounting the bolts 4.

Referring to FIG. 8, during assembly, an upper end portion 1, a plurality of intermediate portions 2 and a lower end portion 3 are arranged successively from top to bottom, and sealing rings 6 are placed between the portions respectively, then secured with the bolts 4 and the nuts 5. The upper end portion 1, the plurality of intermediate portions 2 and the lower end portion 3 thereby form a chamber of the assembled bioreactor chamber.

The invention claimed is:

1. An assembled bioreactor chamber suitable for perfusion culture, said bioreactor chamber comprising an upper end portion, one or more intermediate portions and a lower end portion which are successively connected, and said upper end portion, said one or more intermediate portions and said lower end portion forming a chamber of the assembled bioreactor chamber, wherein said upper end portion is provided with an upper end portion interface for connecting with a culture medium line, said lower end portion is provided with a lower end portion interface for connecting with a culture medium line, and the upper end portion and the one or more intermediate portions are detachably connected in a sealed manner, the one or more intermediate portions and the lower end portion are detachably connected in a sealed manner, and when the number of the one or more intermediate portions is ≥2, adjacent intermediate portions are detachably connected with each other in a sealed manner; wherein at least one barrier sheet is integrated onto the one or more intermediate portions for changing the flow direction of a culture medium, wherein said assembled bioreactor chamber is a fixed bed bioreactor chamber or a fluidized bed bioreactor chamber.

2. The assembled bioreactor chamber according to claim 1, wherein said assembled bioreactor chamber comprises bolts and nuts for integrally securing said upper end portion, said one or more intermediate portions and said lower end portion.

3. The assembled bioreactor chamber according to claim 2, wherein said assembled bioreactor chamber further comprises plug-in slots and plugs which are matched to each other, said plug-in slots and said plugs are provided on connecting end faces of said upper end portion, said one or more intermediate portions and said lower end portion.

4. The assembled bioreactor chamber according to claim 3, wherein said plug-in slots extend inwardly and perpendicularly to the end faces and show an L-shape, and said plugs extend outwardly and perpendicularly to the end faces and show an L-shape.

5. The assembled bioreactor chamber according to claim 3, wherein the number of the one or more intermediate portions of said assembled bioreactor chamber is ≥2, and said assembled bioreactor chamber comprises two kinds of intermediate portions having different internal space volumes, with a ratio of the internal space volume of one kind of intermediate portion to the internal space volume of the other kind of intermediate portion being from 1:2 to 1:5.

6. The assembled bioreactor chamber according to claim 3, wherein said assembled bioreactor chamber is a fixed bed bioreactor chamber, said one or more intermediate portions are provided with a basket for supporting cell growth, and said basket is filled with a cell carrier for cell attachment growth.

7. The assembled bioreactor chamber according to claim 2, wherein the number of the one or more intermediate portions of said assembled bioreactor chamber is ≥2, and said assembled bioreactor chamber comprises two kinds of intermediate portions having different internal space volumes, with a ratio of the internal space volume of one kind of intermediate portion to the internal space volume of the other kind of intermediate portion being from 1:2 to 1:5.

8. The assembled bioreactor chamber according to claim 2, wherein said assembled bioreactor chamber is a fixed bed bioreactor chamber, said one or more intermediate portions are provided with a basket for supporting cell growth, and said basket is filled with a cell carrier for cell attachment growth.

9. The assembled bioreactor chamber according to claim 2, wherein, said at least one barrier sheet is provided within the chamber and arranged in such a staggered manner that the culture medium forms a zigzag flow in the chamber.

10. The assembled bioreactor chamber according to claim 1, wherein the number of the one or more intermediate portions of said assembled bioreactor chamber is ≥2, and said assembled bioreactor chamber comprises two kinds of intermediate portions having different internal space volumes, with a ratio of the internal space volume of one kind of intermediate portion to the internal space volume of the other kind of intermediate portion being from 1:2 to 1:5.

11. The assembled bioreactor chamber according to claim 10, wherein the ratio of the number of the intermediate portions having a larger internal space volume to the number of the intermediate portions having a smaller internal space volume is from 1:1 to 1:5.

12. The assembled bioreactor chamber according to claim 10, wherein said assembled bioreactor chamber is a fixed bed bioreactor chamber, said one or more intermediate portions are provided with a basket for supporting cell growth, and said basket is filled with a cell carrier for cell attachment growth.

13. The assembled bioreactor chamber according to claim 1, wherein said assembled bioreactor chamber is a fixed bed bioreactor chamber, said one or more intermediate portions are provided with a basket for supporting cell growth, and said basket is filled with a cell carrier for cell attachment growth.

14. The assembled bioreactor chamber according to claim 13, wherein the cell carrier is a polyester fiber carrier, a polystyrene fiber carrier, a porous polymer material carrier or a porous ceramic material carrier.

15. The assembled bioreactor chamber according to claim 1, wherein, said at least one barrier sheet is provided within the chamber and arranged in such a staggered manner that the culture medium forms a zigzag flow in the chamber.

16. The assembled bioreactor chamber according to claim 15, wherein the length of said at least one barrier sheet is from 6/10 to 9/10 times a cross-sectional dimension of the chamber.

17. The assembled bioreactor chamber according to claim 15, wherein the length of said at least one barrier sheet is 4/5 times a cross-sectional dimension of the chamber.

18. The assembled bioreactor chamber according to claim 1, wherein said assembled bioreactor chamber further comprises sealing rings for connecting said upper end portion, said one or more intermediate portions and said lower end portion in a sealed manner.

19. The assembled bioreactor chamber according to claim 1, wherein the number of the at least one barrier sheet is equal to or less than the number of the one or more intermediate portions.

20. An assembled bioreactor chamber suitable for perfusion culture, said bioreactor chamber comprising an upper end portion, one or more intermediate portions and a lower end portion which are successively connected, and said upper end portion, said one or more intermediate portions and said lower end portion forming a chamber of the assembled bioreactor chamber, wherein said upper end portion is provided with an upper end portion interface for connecting with a culture medium line, said lower end portion is provided with a lower end portion interface for connecting with a culture medium line, and the upper end portion and the one or more intermediate portions are detachably connected in a sealed manner, the one or more intermediate portions and the lower end portion are detachably connected in a sealed manner, and when the number of the one or more intermediate portions is ≥2, adjacent intermediate portions are detachably connected with each other in a sealed manner; wherein at least one barrier sheet is integrated onto the one or more intermediate portions for changing the flow direction of a culture medium, wherein the number of the at least one barrier sheet is equal to or less than the number of the one or more intermediate portions.

* * * * *

UNITED STATES PATENT AND TRADEMARK OFFICE
CERTIFICATE OF CORRECTION

PATENT NO.        : 11,198,840 B2
APPLICATION NO.   : 16/060336
DATED             : December 14, 2021
INVENTOR(S)       : Q. Liu et al.

It is certified that error appears in the above-identified patent and that said Letters Patent is hereby corrected as shown below:

On the Title Page

Item (54) and in the Specification, Column 1, Line 1, (Title) change "ASSEMBLED" to -- AN ASSEMBLED --

Signed and Sealed this
Twentieth Day of December, 2022

Katherine Kelly Vidal
*Director of the United States Patent and Trademark Office*